(12) United States Patent
Farrell

(10) Patent No.: US 7,351,195 B2
(45) Date of Patent: Apr. 1, 2008

(54) INCONTINENCE INHIBITING OR PREVENTION DEVICE

(75) Inventor: Scott A. Farrell, Halifax (CA)

(73) Assignee: EastMed Incorporated, Nova Scotia (CA)

( * ) Notice: Subject to any disclaimer, the term of this patent is extended or adjusted under 35 U.S.C. 154(b) by 584 days.

(21) Appl. No.: 10/475,824

(22) PCT Filed: Jan. 31, 2003

(86) PCT No.: PCT/CA03/00124

§ 371 (c)(1),
(2), (4) Date: Oct. 22, 2003

(87) PCT Pub. No.: WO03/068105

PCT Pub. Date: Aug. 21, 2003

(65) Prior Publication Data

US 2004/0249238 A1   Dec. 9, 2004

(30) Foreign Application Priority Data

Feb. 15, 2002   (CA) ..................................... 2371974

(51) Int. Cl.
*A61F 2/00* (2006.01)
*A61F 2/02* (2006.01)

(52) U.S. Cl. .......................................................... 600/29

(58) Field of Classification Search ............ 600/29–31, 600/37; 128/885, 830–841; 604/279, 517, 604/544

See application file for complete search history.

(56) References Cited

U.S. PATENT DOCUMENTS

| 4,139,006 | A |   | 2/1979 | Corey |
| 4,920,986 | A |   | 5/1990 | Biswas |
| 5,036,867 | A |   | 8/1991 | Biswas |
| 5,386,836 | A |   | 2/1995 | Biswas |
| 5,618,256 | A | * | 4/1997 | Reimer ........................ 600/29 |
| 6,042,536 | A |   | 3/2000 | Tihon et al. |
| 6,090,098 | A |   | 7/2000 | Zunker et al. |
| 6,110,101 | A |   | 8/2000 | Tihon et al. |
| 6,418,930 | B1 | * | 7/2002 | Fowler ........................ 128/830 |
| 6,530,879 | B1 | * | 3/2003 | Adamkiewicz .............. 600/30 |
| 6,695,763 | B2 | * | 2/2004 | Zunker et al. ................ 600/29 |
| 6,739,340 | B1 | * | 5/2004 | Jensen et al. ................ 128/885 |

FOREIGN PATENT DOCUMENTS

| CA | 1322308 | 9/1993 |
| CA | 1322913 | 10/1993 |
| CA | 2287306 | 11/1998 |
| CA | 2167280 | 1/2005 |

OTHER PUBLICATIONS

Webster's New World Dictionary, Second College Edition, Copyright 1976, William Collins + World Publishing Co., Inc., Cleveland OH, pp. 292-293.

* cited by examiner

*Primary Examiner*—Charles A. Marmor, II
*Assistant Examiner*—Christine D Hopkins
(74) *Attorney, Agent, or Firm*—Schmeiser, Olsen & Watts LLP

(57) ABSTRACT

An incontinence inhibiting or prevention device is provided which can be inserted into the vagina by a wearer without complicated manipulation or folding of the device. The incontinence inhibiting or prevention device helps inhibit or prevent involuntary urination, including that which is stimulated by such bodily functions as coughing and sneezing, while allowing voluntary urination. The device may therefore be worn daily during normal activities and left in place for several days or weeks.

18 Claims, 2 Drawing Sheets

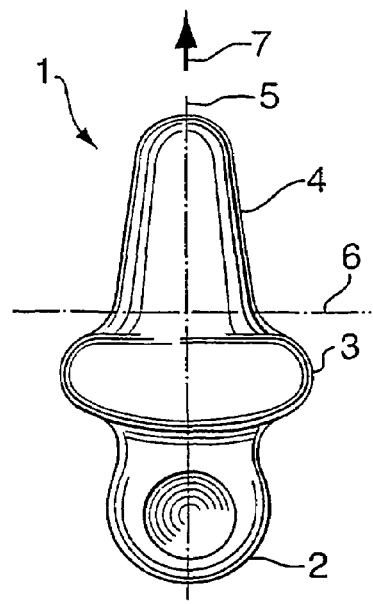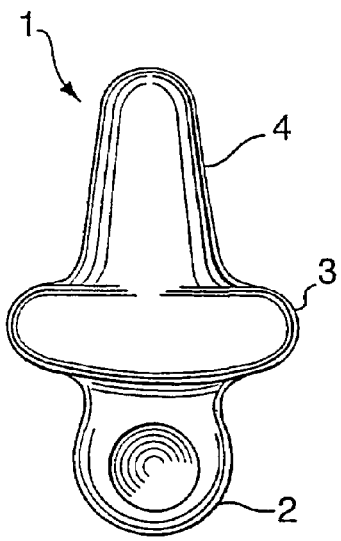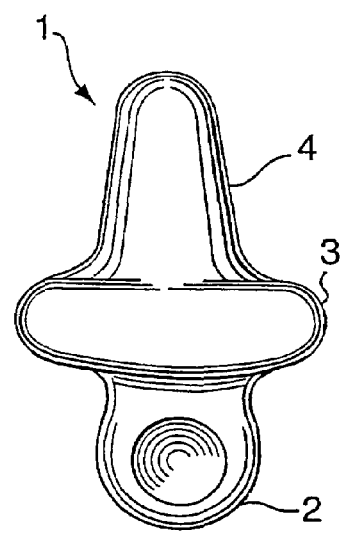
FIG.1　　　FIG.2　　　FIG.3
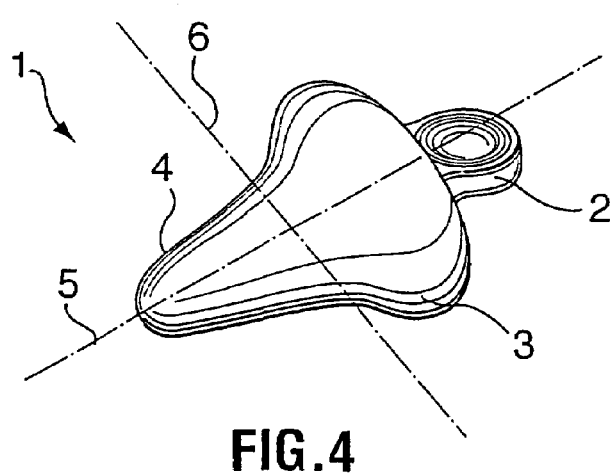
FIG.4

INCONTINENCE INHIBITING OR PREVENTION DEVICE

Various devices are known for inhibiting or preventing urinary incontinence in women. One main class of incontinence inhibiting or prevention device includes devices which are located in the opening of the urethra and block same. Shortcomings of these types of devices include the fact that they must be removed in order to empty the bladder and replaced with a new device which proves inconvenient and costly, they are susceptible to causing infection, and they often cause irritation to body tissue.

Another class of incontinence inhibiting or prevention device includes devices which catch and/or absorb urine, such as diapers or pads. Shortcomings of these types of devices include the fact that they do not provide a woman with any sense of control over the problem of incontinence and that they must be replaced regularly at significant cost.

A third class of incontinence inhibiting or prevention device includes devices which are placed into the vagina to provide support to the urethra to inhibit or prevent the loss of urine, including loss of urine upon coughing or sneezing. This third class of device may be left in place during normal activities and allows for voluntary urination. These devices are normally prescribed and fitted by a health care professional and require regular visits to a health care professional for assessment. Although women are able to learn to remove and insert these devices, the current products are mostly configured such that many women find this task difficult. Conventional devices in this third class of device may be made by casting into a particular shape, such as a ring formed with knobs, and must be folded or otherwise manipulated for insertion, are difficult to reach for removal, or are made such that they expand upon insertion into the vagina and must be removed regularly, usually daily, to avoid the risk of infection.

It is therefore an object of the present invention to provide an incontinence inhibiting or prevention device which can be inserted into the vagina without complicated manipulation or folding of the device. The incontinence inhibiting or prevention device helps inhibit or prevent involuntary urination including that which is stimulated by such bodily functions as coughing and sneezing, while allowing voluntary urination. It is a further object to provide a device which may be worn daily during normal activities and left in place for several days or weeks at a time.

According to an aspect of the present invention there is provided an intra-vaginal incontinence inhibiting or prevention device adapted to be inserted into a vagina, the device comprising a bulbous portion for supporting a female urethra by contacting the vaginal wall beneath the urethra when the device is in position in the vagina, and means adapted to cooperate with the bulbous portion for facilitating insertion, repositioning and removal of the device, the device being capable of substantially retaining its size and shape during insertion of, repositioning within, and removal from, the vagina and when the device is in position in the vagina.

According to another aspect of the present invention there is provided method of inserting an incontinence inhibiting or prevention device as described herein, comprising the steps of separating the labia of the user's vulva and manually inserting the incontinence inhibiting or prevention device into the vagina by way of the handle portion, wherein the incontinence inhibiting or prevention device substantially retains its size and shape during insertion of said device and during use of the device.

According to yet another aspect of the present invention there is provided a method of removing an incontinence inhibiting or prevention device as described herein, from the vagina of a user, comprising the steps of separating the labia of the user's vulva, gripping the incontinence inhibiting or prevention device by the handle portion, and pulling the incontinence inhibiting or prevention device out of the user's vagina, wherein the incontinence inhibiting or prevention device substantially retains its size and shape during removal of said device.

According to still another aspect of the present invention there is provided a set of incontinence inhibiting or prevention devices as described above, each incontinence inhibiting or prevention device of the set being of a different size, whereby to permit selection of a best fit to inhibit or prevent incontinence and allow for a patient to readily change to a smaller or larger incontinence inhibiting or prevention device.

Embodiments of the invention will now be described, by way of example, with reference to the accompanying drawings, in which:

FIG. 1 is a plan view of an incontinence inhibiting or prevention device according to an embodiment of the present invention;

FIG. 2 is a plan view of an incontinence inhibiting or prevention device according to a second embodiment of the present invention;

FIG. 3 is a plan view of an incontinence inhibiting or prevention device according to a third embodiment of the present invention;

FIG. 4 is a perspective view of the incontinence inhibiting or prevention device of FIG. 1.

DESCRIPTION OF THE PREFERRED EMBODIMENTS

Figure 5:
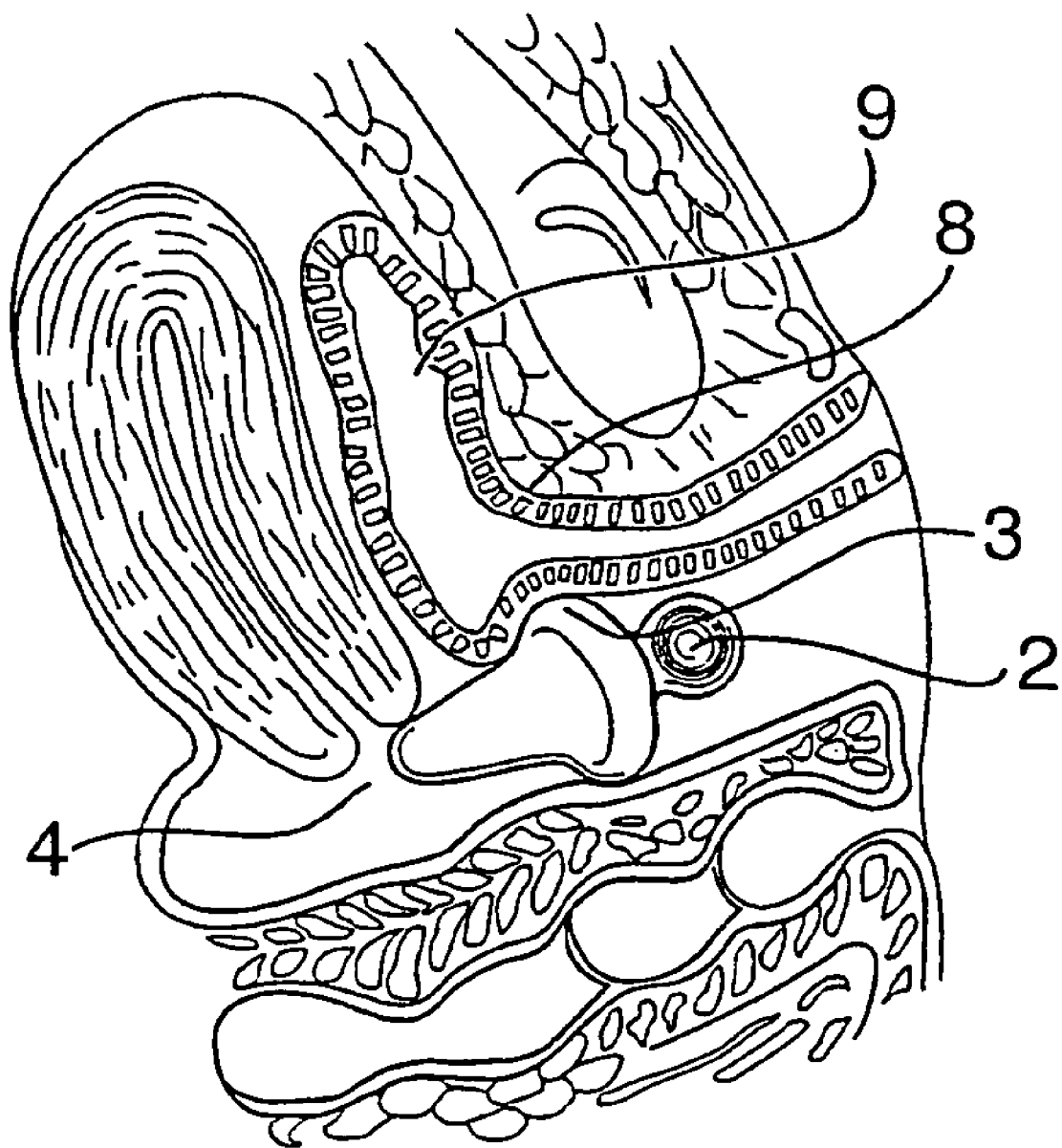
FIG. 5 is a diagrammatic representation of the incontinence inhibiting or prevention device according to an embodiment of the present invention as positioned in a user.

Preferred embodiments of the present invention are described below with reference to FIGS. 1 to 5. An incontinence inhibiting or prevention device 1 as seen in FIGS. 1 to 4 may be described as having three principal portions, a handle portion 2, a bulbous portion 3 and a leading portion 4. It is, however, understood that these portions preferably form one continuous device 1, such segmentation being intended for illustrative and descriptive purposes. FIG. 1 illustrates a device according to an embodiment of the present invention. FIG. 2 illustrates a device according to a second embodiment of the present invention having a wider bulbous portion and a length less than the device shown in FIG. 1. FIG. 3 illustrates a device according to a third embodiment of the present invention having a wider bulbous portion and a lesser length than the device show in FIG. 2. The principal purpose of the bulbous portion 3 is to come into contact with, and support, the urethra of a woman in order to inhibit or prevent involuntary urination including incidences stimulated by such bodily functions as coughing and sneezing. The bulbous portion 3 has attached thereto on either side, the handle portion 2 and the leading portion 4, respectively. A longitudinal axis 5 and lateral axis 6 is illustrated on both FIGS. 1 and 4 and are defined such that lateral axes, one of which being lateral axis 6, are substantially perpendicular to the longitudinal axis 5. The bulbous portion 3 is preferably circular and symmetric about the longitudinal axis 5 thus permitting rotation of the device to occur about the longitudinal axis 5 without compromising the functioning of the device. The direction of insertion of the device into the vagina is indicated by reference numeral 7 and is substantially parallel to the longitudinal axis 5.

Extending along the longitudinal axis 5 from the bulbous portion 3 toward the handle portion 2, the lateral dimensions of the device decrease until the handle portion 2 is reached. One purpose of the handle portion 2 is to permit the insertion, repositioning, and removal of the device into and from the vagina. This decrease in lateral dimensions between bulbous portion 3 and handle portion 2 is to facilitate insertion and removal of the device 1. The handle portion 2 is preferably of a shape which facilitates gripping by a hand or the like. As seen from FIG. 4 a preferred shape of the handle portion is concave to facilitate gripping by a patient.

Extending from the bulbous portion 3 along the longitudinal axis 5 toward the leading portion 4, the lateral dimensions of the device decrease. The leading portion 4 is preferably of conical shape with a rounded forward end. In this configuration, the leading portion 4 facilitates insertion and removal of the device 1. Both the handle portion 2 and the leading portion 4 are smaller in lateral dimensions than the bulbous portion 3.

FIG. 5 illustrates an incontinence inhibiting or prevention device which is in place in the vagina. As seen from this drawing the internal wall of the vagina is in contact with the incontinence inhibiting or prevention device 1 and is pushed outwardly to support the urethra 8 and thereby limit or prevent involuntary passage of urine from the bladder 9, which is also shown in FIG. 5.

The device is purposed to allow voluntary urination and may be left in place during normal day-to-day activities, overnight and for several days. The device is washable and may be re-used. The device may be manually inserted, repositioned, and removed by a user. Frequent visits to health care professionals are thus not necessary in most cases. The size and shape of the device are substantially non-variable during use, including insertion, repositioning and removal of the device.

According to an embodiment of the present invention the device may be formed with a bulbous portion and a receiving portion which may receive a handle or an applicator. In this way, a handle or an applicator may be removably connected to the device for insertion, repositioning or removal of the device.

The handle portion may act as a push button thereby being capable of being pushed substantially into the incontinence inhibiting or prevention device and released by being pushed again.

The device may be made in a plurality of sizes or may be custom made to fit each particular case. The material used for the device is preferably a medical grade plastic. In a preferred embodiment of the present invention, three standard sizes are provided, i.e. small, medium and large as are proportionally represented in FIGS. 1, 2 and 3 respectively. The diameter of the bulbous portion may be, respectively, 3.8, 4.3 and 4.8 cm and the overall length of the device 7.0, 6.9 and 6.8 cm. The three standard sizes may be provided together in a container or storage case as a fitting set. Once the appropriate size is determined this incontinence inhibiting or prevention device may be used by the patient. Individual replacement incontinence inhibiting or prevention devices may be available separately. The storage case may comprise distinct supportive compartments each compartment designed to house one of the incontinence inhibiting or prevention devices such that air can circulate around the incontinence inhibiting or prevention devices to permit evaporation of any moisture remaining after one or more of the incontinence inhibiting or prevention devices have been washed. A lid of the case may fit snugly into the bottom and may include flanges which conform with the shape of each incontinence inhibiting or prevention device thereby ensuring that when the lid is closed the incontinence inhibiting or prevention devices will remain in place during movement of the case, such as during transportation. The lid may be hinged on one side of the case and may be made of transparent plastic.

In addition to permitting a determination of the best initial fit to inhibit or prevent urinary incontinence, the set of three sizes of incontinence inhibiting or prevention device will allow for a patient to move to a larger or smaller incontinence inhibiting or prevention device in order to accommodate changes in the patient's body or needs. For example, if vaginal accommodation occurs, the patient may require a larger incontinence inhibiting or prevention device in order to maintain continence. A smaller incontinence inhibiting or prevention device may, for example, be useful if shrinkage occurs.

Although 3 sizes of the device have been described herein, any number of incontinence inhibiting or prevention devices of varying dimensions could be provided as a set or otherwise.

In order to insert the incontinence inhibiting or prevention device into the vagina, the incontinence inhibiting or prevention device and the vagina are each preferably lubricated with, preferably, a water soluble lubricant, the labia of the vulva then being separated and the incontinence inhibiting or prevention device inserted into the vagina using the handle portion and pushed to a position where the incontinence inhibiting or prevention device sufficiently supports the urethra.

In order to remove the incontinence inhibiting or prevention device, the labia of the vulva are separated, the handle portion is gripped and the incontinence inhibiting or prevention device is pulled out of the vagina.

The incontinence inhibiting or prevention device or set of incontinence inhibiting or prevention devices according to the present invention may be accompanied by a CD-ROM containing instructions in addition to a written instructions manual.

INDUSTRIAL APPLICABILITY

The incontinence inhibiting or prevention device and associated methods and set as disclosed herein generally provide improved means of inhibiting or preventing involuntary urination.

The invention claimed is:

1. An intra-vaginal incontinence inhibiting or prevention device adapted to be inserted into a vagina, said device characterized by:
   a bulbous portion for supporting a female urethra by contacting the vaginal wall beneath the urethra when said device is in position in the vagina; and
   a handle portion connected to said bulbous portion and capable of being gripped by a hand for facilitating insertion, repositioning and removal of said device, wherein said device substantially retains its size and shape during insertion into, repositioning within, and removal from, the vagina and when said device is in position in the vagina.

2. An incontinence inhibiting or prevention device according to claim 1, characterized in that said handle portion is removably connected to said bulbous portion.

3. An incontinence inhibiting or prevention device according to claim 1, characterized in that said handle portion is permanently connected to said bulbous portion.

4. An incontinence inhibiting or prevention device according to claim 1, characterized in that said bulbous portion and said handle portion are centered about a longitudinal axis which is substantially parallel to an intended direction of insertion of said device into the vagina;
lateral dimensions of said bulbous portion decreasing in a direction toward said handle portion; and
in that said lateral dimensions of said bulbous portion are defined as those dimensions that are substantially perpendicular to said longitudinal axis.

5. An incontinence inhibiting or prevention device according to claim 4, further characterized by a leading portion centered about said longitudinal axis, and located in front of said bulbous portion on the opposite side to said handle portion having regard to the intended direction of insertion, the lateral dimensions of said leading portion decreasing in a direction away from said bulbous portion.

6. An incontinence inhibiting or prevention device according to claim 5, characterized in that the lateral dimensions of said bulbous portion decrease in a direction toward said leading portion.

7. An incontinence inhibiting or prevention device according to claim 5, characterized in that said leading portion is of generally conical shape with a rounded tip.

8. An incontinence inhibiting or prevention device according to claim 1, characterized in that said handle portion is concave.

9. An incontinence inhibiting or prevention device according to claim 1, characterized in that said bulbous portion is substantially circular in a plane perpendicular to the intended direction of insertion of said device into a vagina.

10. An incontinence inhibiting or prevention device according to claim 1, characterized in that a diameter of said bulbous portion and a length of said device, is adapted to achieve substantially continuous contact of said bulbous portion with the vaginal wall to effect support of the urethra.

11. An incontinence inhibiting or prevention device according to claim 1, characterized in that said device is made of medical grade plastic material.

12. An incontinence inhibiting or prevention device according to claim 1, characterized in that said handle portion is adapted to be pushed substantially into said incontinence inhibiting or prevention device so as to be recessed therein, and in that said handle portion is adapted to reemerge from said incontinence inhibiting or prevention device upon pressing upon said handle portion.

13. A method of inserting an incontinence inhibiting or prevention device according to claim 1, characterized by comprising the steps of:
separating the labia of the user's vulva; and
manually inserting said incontinence inhibiting or prevention device into the vagina by way of the handle portion, wherein said incontinence inhibiting or prevention device substantially retains its size and shape during insertion of said device and during use of said device.

14. A method of removing an incontinence inhibiting or prevention device according to claim 1 from the vagina of a user, characterized by comprising the steps of:
separating the labia of the user's vulva;
gripping the incontinence inhibiting or prevention device by the handle portion; and
pulling said incontinence inhibiting or prevention device out of the user's vagina, wherein said incontinence inhibiting or prevention device substantially retains its size and shape during removal of said device.

15. A set of incontinence inhibiting or prevention devices according to claim 1, each incontinence inhibiting or prevention device of said set being of a different size, whereby to permit selection of a best fit to inhibit or prevent incontinence and allow for a patient to readily change to a smaller or larger incontinence inhibiting or prevention device.

16. A set of incontinence inhibiting or prevention devices according to claim 15, characterized in that said set comprises three incontinence inhibiting or prevention devices.

17. An incontinence inhibiting or prevention device according to claim 1, characterized in that said handle portion is adapted to be pushed substantially into said bulbous portion so as to be recessed therein, and in that said handle portion is adapted to reemerge from said incontinence inhibiting or prevention device upon pressing upon said handle portion.

18. An incontinence inhibiting or prevention device according to claim 8, characterized in that the handle portion where gripped is concave.

* * * * *